US005571194A

United States Patent [19]
Gabriel

[11] Patent Number: 5,571,194
[45] Date of Patent: Nov. 5, 1996

[54] FEMORAL AUGMENTATION SYSTEM FOR ARTIFICIAL KNEE JOINT

[75] Inventor: Stefan M. Gabriel, Lakeville, Mass.

[73] Assignee: Johnson & Johnson Professional, Inc., Raynham, Mass.

[21] Appl. No.: 339,019

[22] Filed: Nov. 14, 1994

[51] Int. Cl.⁶ .................................................. A61F 2/30
[52] U.S. Cl. .................................... 623/18; 623/20
[58] Field of Search ........................... 623/18, 20

[56] References Cited

U.S. PATENT DOCUMENTS

| | | | |
|---|---|---|---|
| 4,778,473 | 10/1988 | Matthews et al. | 623/20 |
| 4,936,847 | 6/1990 | Manginelli | 623/23 |
| 4,936,853 | 6/1990 | Fabian et al. | 623/20 |
| 4,950,298 | 8/1990 | Gustilo et al. | 623/20 |
| 5,152,796 | 10/1992 | Slamin . | |
| 5,201,769 | 4/1993 | Schutzer | 623/23 |
| 5,222,984 | 6/1993 | Forte | 623/22 |
| 5,344,461 | 9/1994 | Philipot | 623/20 |
| 5,387,241 | 2/1995 | Hayes | 623/20 |

FOREIGN PATENT DOCUMENTS 2223174  4/1990  United Kingdom ...................... 623/20

*Primary Examiner*—Michael J. Milano
*Attorney, Agent, or Firm*—William C. Geary, III; Nutter, McClennen & Fish LLP

[57] ABSTRACT

An augmentation system for a femoral component of a knee prosthesis includes a main augmentation block and a secondary block disposed within the main augmentation block. The secondary block is adjustably positioned within the main augmentation block such that relative motion between the two facilitates easy and secure fixture of the augmentation system within a prosthesis. The augmentation system of the invention can be used with either left or right side prostheses.

21 Claims, 4 Drawing Sheets

FEMORAL AUGMENTATION SYSTEM FOR ARTIFICIAL KNEE JOINT

BACKGROUND OF THE INVENTION

This invention relates to a knee joint prosthesis, and more particularly to a prosthesis useful to augment bone deficiencies during knee arthroplasty procedures.

Knee arthroplasty is a well known surgical procedure by which a diseased and/or damaged natural knee joint is replaced by a prosthetic knee joint. In some instances, due to disease or trauma, insufficient healthy boney mass exists at the distal end of the femur to secure a femoral prostheses. It is thus necessary to remove a portion of the femur to ensure sufficient anchoring and a proper fit for the femoral prosthesis. In these instances, and in other cases, it is necessary to augment the inferior portion of the femoral component of the prosthesis to add additional thickness a prosthesis to compensate for a lack of sufficient boney tissue.

Augmentation of the boney mass can be accomplished by securing augmenting devices to the femoral component. Earlier techniques require that the augmenting devices be cemented to the inferior surface of the femoral component. Such techniques require accurate measurements and a great deal of precision since the augmenting device is difficult, if not impossible, to remove once it is secured to the prosthesis. These techniques do not allow sizing of the proper augmenting device by trial and error.

An improved augmentation technique is described in U.S. Pat. No. 4,936,847 (Manginelli). This patent describes an augmentation system that can be removeably and replaceably secured within a femoral component of a knee joint prosthesis. Such as design is advantageous because it avoids the need to cement augmenting devices to the inferior surface of the femoral component. As a result, augmenting devices of varying thicknesses can be fitted into place on the inferior surface of the femoral component. The augmenting devices can be removed and replaced with devices having different dimensions until the proper augmentation thickness is determined. Such an augmentation system, however, requires a specially constructed femoral component.

Despite existing augmentation systems, there remains a need to provide improved systems that allow standard augmenting components that can easily and securely be affixed within an existing femoral component. The cost of joint prostheses that utilize many current augmentation systems can be quite high due to the scrap rate and because prosthesis components, such as femoral components, must often be specially constructed to accommodate the augmenting devices. There is thus a need for an augmentation system that allows augmenting devices to be easily and securely fitted to standard prosthesis components.

It is thus an object of the invention to provide a femoral augmentation system that securely and easily fits within a femoral component of a knee joint prosthesis. Another object of the invention is to provide a femoral augmentation system that is compatible with standard femoral components of knee joint prostheses. It is also an object to provide an augmentation system that offers a great deal of versatility in that it can be used with different types of femoral components, including cruciate retaining and cruciate sacrificing femoral components. Other objects will be apparent to one of ordinary skill in the art upon reading the description that follows.

SUMMARY OF THE INVENTION

The present invention relates to a femoral augmentation system for use with knee joint prostheses. The system of the present invention serves to provide increased thickness to femoral components where boney deficiencies exist in a patient's femur.

The augmentation system of the invention includes a main augmenting block having a nominal distal surface and proximal surface. The main augmenting block also has first and second side surface that are either anterior or posterior surfaces, and third or fourth side surfaces that are either medial or lateral surfaces. The side surfaces of the main augmenting block can be of varying dimensions to provide desired thickness to the main augmenting block.

The main augmenting block also has at least one surface feature disposed on at least one of the side surfaces. The surface feature can be either an indentation or a protrusion formed in the side surface. Preferably, the surface feature is disposed on the third or fourth side surfaces, and there is present at least one surface feature on or associated with an opposite side surface.

The main augmenting block also includes a channel that extends into an interior portion thereof through one of the side surfaces. The channel is dimensioned to securely fit a secondary block component that is adjustably positioned within the channel. The secondary block component is adapted to be adjusted to secure the augmentation device within a joint prosthesis by an interference fit. The secondary block component preferably includes a side surface that corresponds in shape and orientation to the side surface of the main block through which the channel extends. A screw device is associated with the secondary block component, extending therethrough to effect adjustment of the position of the secondary block means relative to the main augmenting block.

In one embodiment a substantially centrally disposed aperture extends through the main augmenting block from the nominal distal surface to the proximal surface. A removable plug is preferably disposed within the aperture of the main augmenting block, in an interference fit.

The augmenting system of the invention is advantageous because it is able to fit securely within standard designs of knee prostheses femoral components. The augmentation system is used by positioning the system at a suitable location on the inferior surface of a femoral component. The screw that extends into the secondary block component can be used to expand (or contract) the secondary block, relative to the main block, thus changing the overall width of the augmentation device such that the augmentation device securely fits within the femoral component. By so doing, any surface features present on the main augmenting block engage the surface of the femoral component or complimentary surface features of the femoral component, to create a secure interference fit.

The "nominal distal surface" is defined herein as the entire surface area of the distal surface of the main augmenting block if the channel positioned within the main augmenting block does not form a cutout within the distal surface. If the channel does form a cutout of the portion of the distal surface of the main block, the "nominal distal surface" is defined to include the entire distal surface of the main block as well as the cutout portion of the distal surface of the main block.

BRIEF DESCRIPTION OF THE DRAWINGS

For a further understanding of the nature and objects of the invention, reference should be made to the following detailed description of the invention and to the accompanying drawings, in which.

DETAILED DESCRIPTION OF THE INVENTION

Figure 1:
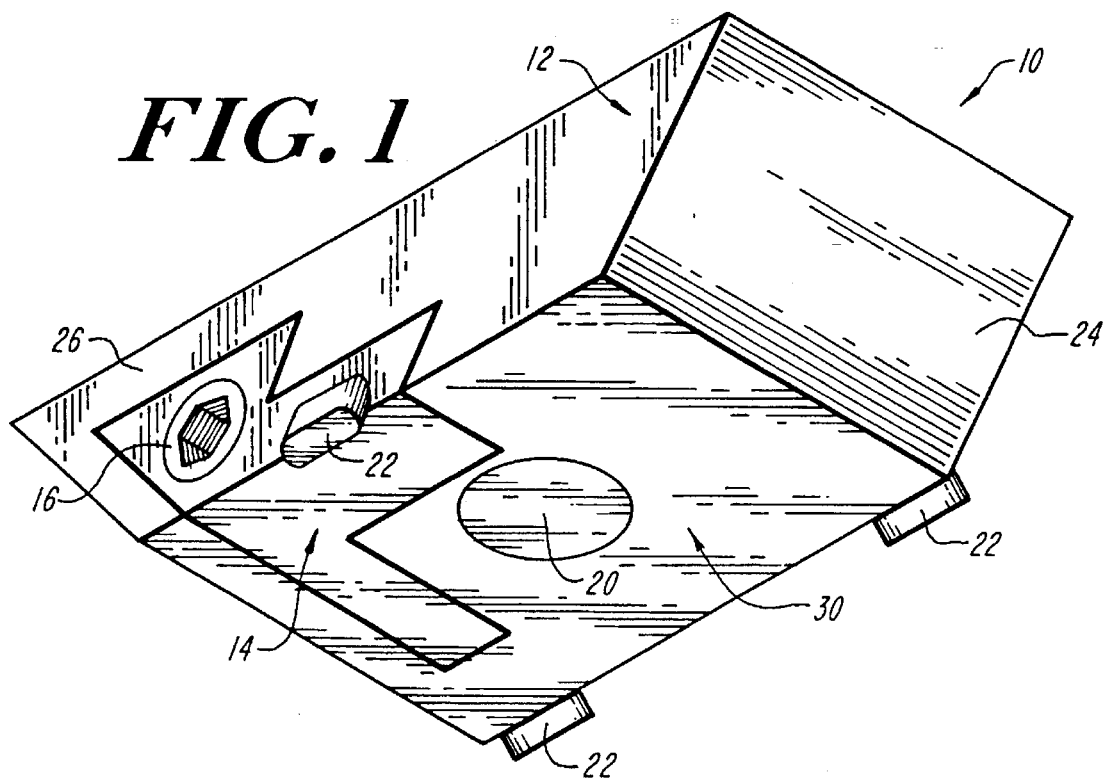
FIG. 1 is a perspective view of an augmentation system designed according to the present invention and intended to fit in a distal portion of a knee prosthesis femoral component.
Figure 2:
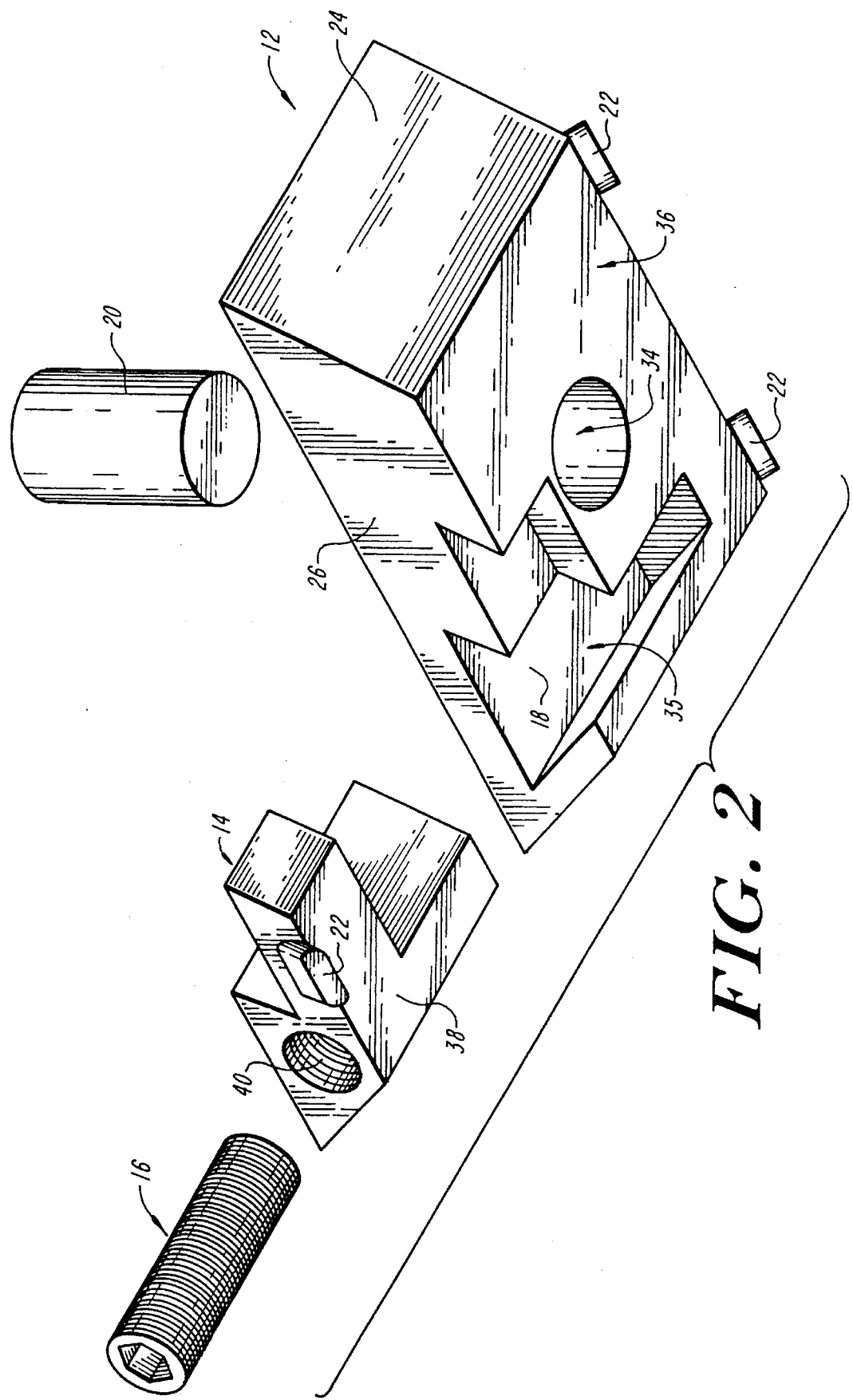
FIG. 2 is an exploded view of the augmentation system illustrated in FIG. 1.

As illustrated in FIGS. 1 and 2, the augmentation system 10 includes a main augmentation block 12 within which is disposed a channel 18. A secondary augmentation block 14 is disposed within channel 18 and includes a screw 16 or similar device to adjust the position of the secondary augmentation block 14 with respect to the main augmentation block 12. Surface features 22, which may be protrusions or indentations, preferably are disposed on one or more surfaces of the main augmentation block 12 or the secondary augmentation block 14.

Figure 9:
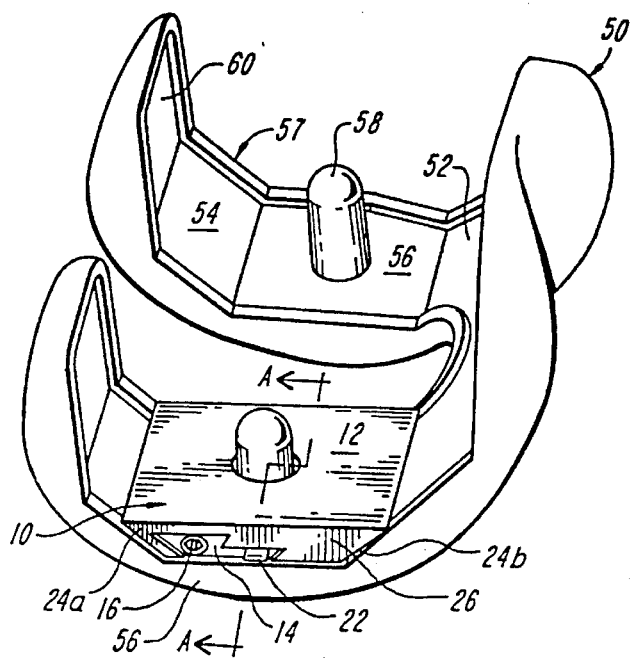
FIG. 9 illustrates the positioning of an augmentation system of the type shown in FIG. 1 within a distal portion of the femoral component of a knee prosthesis.

In one embodiment the augmentation system includes a removable plug 20 disposed within an aperture 34 of the main augmentation block. Plug 20 and aperture 34 enable the augmentation system 10 of the invention to be used with both cruciate sacrificing and cruciate retaining knee femoral components. When the augmentation system 10 is used with a cruciate sacrificing femoral component, the plug 20 remains secure within aperture 34. When the augmentation system 10 of the invention is used with a cruciate retaining femoral component, the plug 20 is removed from main block 12 and pegs 58 can be inserted through the aperture 34, as shown in FIG. 9.

Figure 3:
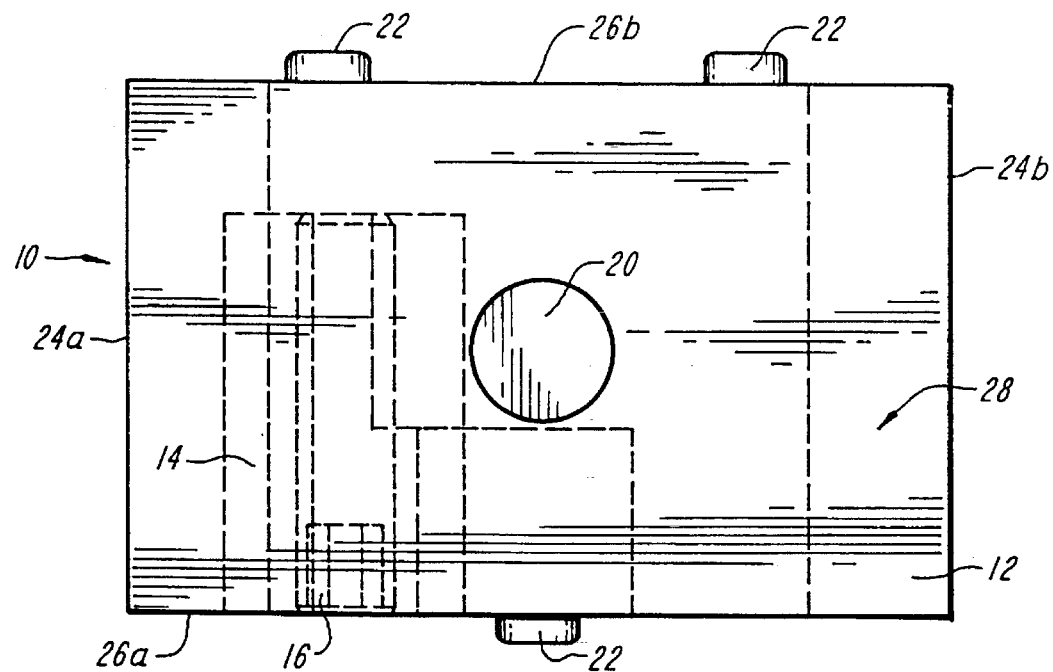
FIG. 3 is a top view of the augmentation system illustrated in FIG. 1.
Figure 4A:
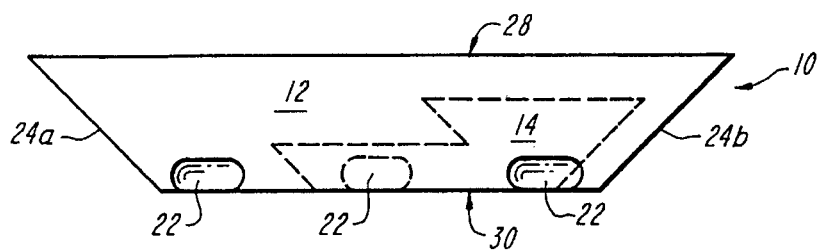
FIG. 4A is a side view, from the medial or lateral side, of an alternative augmentation system having indented surface features.
Figure 4:
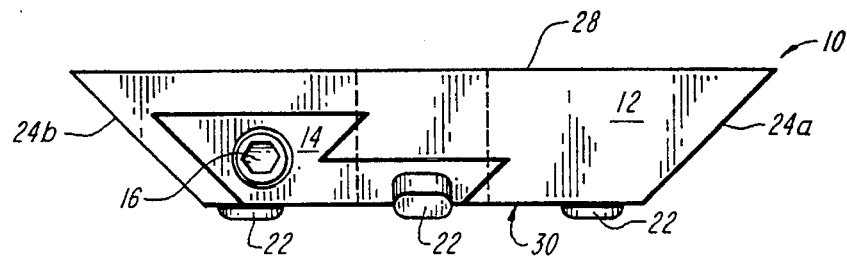
FIG. 4 is a side view, from the medial or lateral side, of the augmentation system illustrated in FIG. 1.
Figure 5:
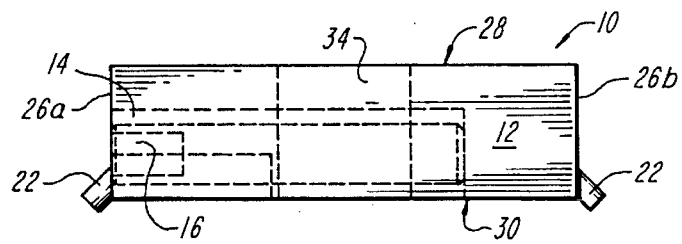
FIG. 5 is a side view, from the anterior or posterior side, of the augmentation system illustrated in FIG. 1.

The augmentation system 10 of the present invention is able to be used, without modification, in either left or right side knee prostheses. As shown in FIGS. 3 through 5, the main block 12 of the augmentation system 10 has a proximal surface 28 and nominal distal surface 30. The area of the proximal surface 28 is preferably greater than the area of the nominal distal surface 30.

First and second side surfaces 24a, 24b of the main block 12 can be anterior or posterior surfaces, depending upon whether the augmentation system is used with a left or right side prosthesis. Preferably, first and second side surfaces 24a, 24b are canted such that each of the first and second side surfaces slope inwardly from the proximal surface 28 to the nominal distal surface 30 as shown in FIG. 4. The angle of the first and second side surfaces 24a, 24b can vary as will be appreciated by those having ordinary skill in the art. As shown in FIG. 9, the angle of these surfaces corresponds to the angles of the anterior and posterior chamfers 52, 54 of a femoral component to enable proper seating of the augmentation system 10 within a femoral component.

The third and fourth side surfaces 26a, 26b of the augmentation system 10 correspond to either medial or lateral facing surfaces, depending upon whether the augmentation system is used in a left or right side knee prosthesis. Side surfaces 26a, 26b preferably are substantially vertical.

As illustrated, channel 18 extends into the main block 12 through one of the side surfaces of the main block. Preferably, the channel 18 extends through one of the third or fourth side surfaces, 26a 26b. The channel 18 can assume virtually any desired shape, but in a preferred embodiment, illustrated in FIGS. 1, 2 and 3, the channel is generally L-shaped. The channel 18 may extend into the main block 12 between the proximal 28 and nominal distal surfaces 30 of the main block. Alternatively, as illustrated in FIG. 2, the channel 18 extends into the main block 12 such that it forms a cutout 35 of the actual distal surface 36 of the main block 12. In this embodiment the actual distal surface 36 and the distal surface 38 of secondary block 14 together form the nominal distal surface 30 the main block 12.

Secondary block 14 is configured and dimensioned to adjustably fit within channel 18. A threaded screw 16 or similar adjusting device is positioned within the threaded bore 40 of the secondary block 14. Adjustment of the screw 16 causes the distal end of the screw to abut the end wall (not shown) of channel 18. Further manipulation of the screw 16 in the same direction causes the secondary block 14 to move away from the main block 12, effectively increasing the overall width of the augmentation system 10. Manipulation of the screw 16 in the opposite direction causes the secondary block 14 to move back towards the main block 12, decreasing the overall width of the augmentation system 10.

The secondary block 14 includes a side surface 32 which corresponds in shape and orientation to the side surface of the main block 12 through which the channel 18 extends. Thus, in one configuration the side surface 32 of the secondary block can be substantially flush with one of the side surfaces of the main block 12, such as third or fourth side surface 26a, 26b.

The main block 12 preferably includes at least one surface feature 22 disposed on at least one of the side surfaces of the main block. In one embodiment the surface features are disposed on at least one of the third or fourth side surfaces 26a, 26b. In the embodiment illustrated in FIGS. 1 through 3, two surface features 22 are disposed on either of the third or fourth side surfaces 26a, 26b which is the side surface of the main block opposite the side surface through which channel 18 extends. In this configuration a surface feature 22 appears on the side surface 32 of secondary block 14. The surface features, which may be indentations or protrusions, are intended to cooperate with structures of a knee prosthesis femoral component in order to provide secure mounting of the augmentation system 10 within a femoral component. Thus, one of ordinary skill in the art will appreciate that the number and placement of the surface features can be varied to optimize the fixture of the augmentation system 10 within a femoral component.

As noted above, the surface features 22 can be indentations or protrusions. Indented surface features 22, shown in FIG. 4A, can extend into the structure, that is either the main block or the secondary block, in a non-angled manner or in an angled manner. Preferably, the indentations can be of varied dimensions, but preferably have a depth of about 1 to 2 mm and a length or diameter of approximately 1 to 2 mm. Protruding surface features can extend out from the structure in a non-angled manner or at an angled manner. A preferred angled protruded surface feature extends outwardly and distally of the structure. Preferably, surface feature protrusions have a length of about 1 to 2 mm and extend out from the structure by about 1 to 2 mm.

Plug 20, as noted above, is removeably and replaceably positioned within aperture 34 of the main block 12. The plug 20 can remain in or be removed from the augmentation system 10 depending upon whether the augmentation system is used with a cruciate retaining or a cruciate sacrificing femoral component of a knee prosthesis. The aperture 34 preferably is circular in shape having a diameter of approximately 5 to 7 mm. The plug 20 is of a corresponding shape and dimension so as to enable it to fit securely, in an interference fit, within aperture 34. Preferably, the plug 20 is made from ultra high molecular weight polyethylene or other suitable materials.

Figure 6:
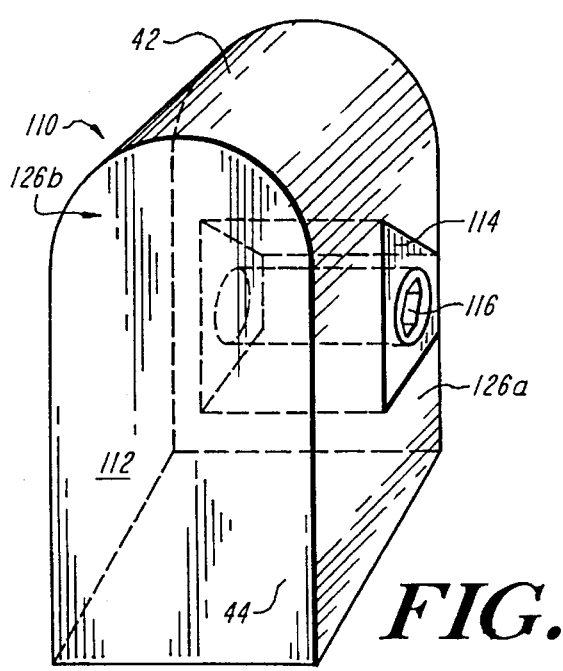
FIG. 6 is a perspective view of an alternative augmentation system according to the present invention designed to fit in a posterior portion of a knee prosthesis femoral component.
Figure 7:
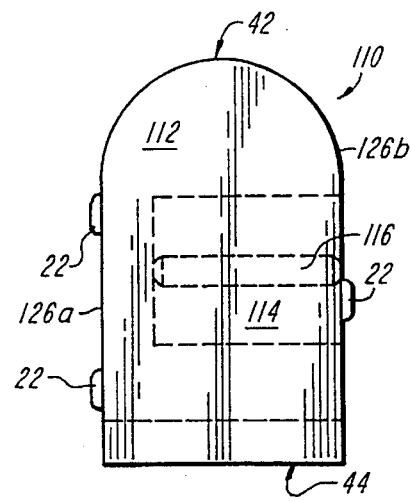
FIG. 7 is a side view, from the anterior or posterior side of the augmentation system illustrated in FIG. 6.
Figure 8:
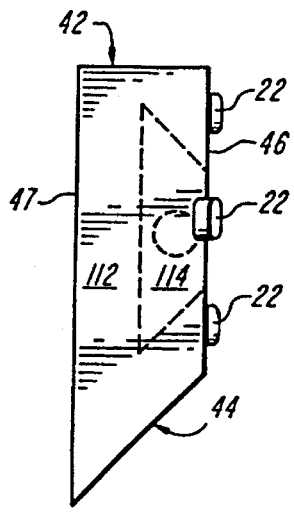
FIG. 8 is a side view, from the lateral or medial side, of the augmentation system of FIG. 6.

FIGS. 6 through 8 illustrate a configuration for an alternative augmentation system 110 of the present invention. This configuration system is best suited for augmentation of a posterior portion of the femoral component of a knee prosthesis.

In this embodiment, the augmentation system also includes a main block 112 having a secondary block 114 mounted within a channel 118 that extends into the interior of the main block. A screw 116 or similar device extends into the secondary block 116 to control the positioning of the secondary block with respect to the main block.

The alternative augmentation system 110, illustrated in FIGS. 6 through 8, has a slightly different shape and surface configuration than does the main block 12 shown in FIGS. 1 through 5. As illustrated in FIG. 6 the proximal surface 128 of main block 112 is convex or dome-like while the distal surface 44 is canted.

Preferably, the distal surface 44 is angled such that it extends downwardly from a shorter posterior side surface 46 to a longer anterior side surface 47. The angle of the distal surface 44 should be substantially equivalent to the angle of the posterior chamfer 54 of a femoral component 50 upon which the distal surface 44 of the main block 112 is intended to seat. One of ordinary skill in the art will appreciate that this angle can be in the range of about 2° to 90° and is preferably about 45°.

As noted above, the posterior side surface 46 is slightly shorter than the anterior side surface 47. Posterior and anterior side surfaces 46, 47 preferably are substantially vertical in orientation.

The main block 12 of the alternative augmentation system further includes third and fourth side surfaces 126a, 126b, which may be lateral or medial surfaces. Side surfaces 126a, 126b are substantially vertical in orientation.

The secondary block 114 of augmentation system 110 extends into the main block 114 through either of the side surfaces 126a, 126b, and is disposed within a channel (not shown) similar to channel 18. In addition, surface features 122 may be used in connection with this embodiment of an augmentation block in a manner similar to that described above. Surface features 122 may be indentations or protrusions and share the same characteristics of and may be positioned similar to surface features 22 discussed above.

Figure 9A:
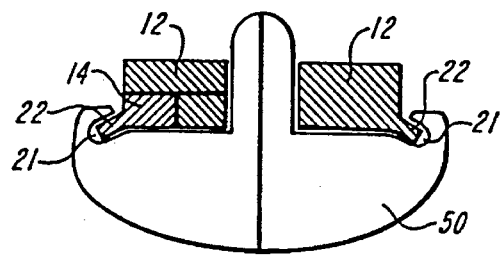
FIG. 9A is a sectional view of the augmentation system shown in FIG. 9, along lines A—A, showing the engagement of the augmentation system within a femoral component.

FIGS. 9 and 9A illustrate the positioning of augmentation system 10 within a femoral component 50 of a knee prosthesis. In the illustrated embodiment the femoral component 50 is a cruciate retaining femoral component and includes pegs 58 which extend from the inferior surface of the lateral condyle 56 and the medial condyle 57. The femoral component further includes an anterior chamfer 52 and a posterior chamfer 54.

Before mounting augmentation system 10 within a cruciate retaining femoral component 50, the plug 20 is removed from aperture 34. The augmentation system is then mounted by inserting the peg 58 which extends from the lateral condyle 56 through aperture 34. As so positioned, the nominal distal surface 30 of augmentation system 10 abuts the inferior surface of lateral condyle 56 while the posterior side surface 24a and the internal side surface 24b of the main augmentation block 12 abut the posterior chamfer and the anterior chamfer, respectively. As shown in FIG. 9A surface features 22 engage complementary structures 21 within femoral component 50 to secure the augmentation system in place. Manipulation of screw 16 can extend the secondary block 14 to an extent sufficient to ensure a secure fit for the augmentation system 10.

Figure 10:
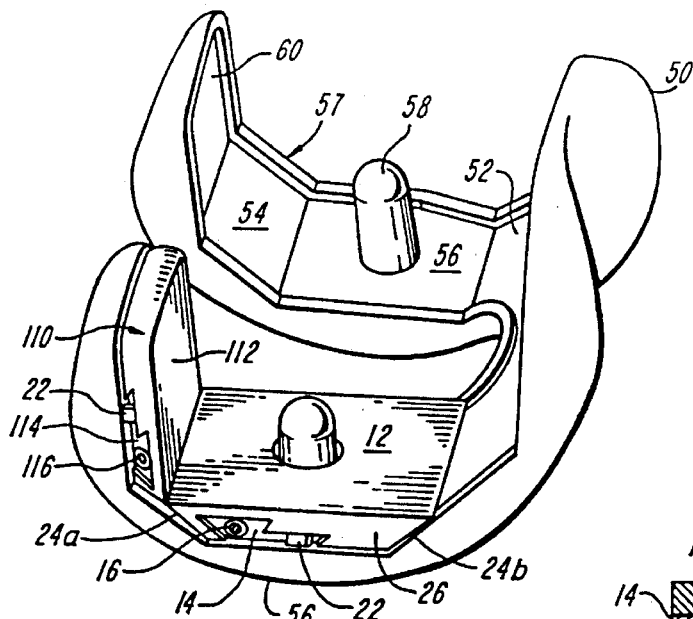
FIG. 10 illustrates the positioning of an augmentation system of the type shown in FIG. 6 within the posterior portion of the femoral component of a knee prosthesis.

FIG. 10 illustrates the positioning of an augmentation system 110, which is intended for mounting in a posterior portion of a femoral component in order to allow for build up of the posterior inner condylar surfaces of a femoral component.

As illustrated, the augmentation system 110 is positioned against the inferior surfaces of posterior chamfer 54 and posterior flange or condyle 60. The distal surface 44 of main block 112 abuts the posterior chamfer 54 while the posterior side surface 46 abuts the inferior surface of the posterior flange or condyle 60.

The dimensions of the augmentation system of the invention can vary as required by the dimensions of the joint prostheses with which the system is to be used. One of ordinary skill in the art will be able to determine the proper dimensions of the augmentation systems 10, 110 of the invention so as to closely fit the configuration of the interior of a femoral component with which it is used. Generally, the thickness (proximal to distal) of the augmentation system is in the range of approximately 2 to 20 millimeters while the width (medial to lateral) ranges from about 10 mm to 40 mm and the length (anterior to posterior) ranges from about 10 mm to 60 mm.

The augmentation system of the invention can be made from a variety of biocompatible materials having high strength, durability and resistance to wear debris. Examples of such materials include metal alloys such as cobalt chromium alloy, titanium vanadium alloy, stainless steel, ceramics and other materials that are well known for use in the manufacture of implantable bone prostheses.

The augmentation system of the invention offers many advantages. For example, the augmentation system is able to be secured to knee prostheses components, without bone cement, in a secure fit such that relative motion between the joint prosthesis and augmentation system is relatively low or non-existent. This secure fit ensures that the performance of the augmented prosthesis component is not compromised. Moreover, the augmentation system of the invention can be easily attached within a joint prosthesis. Of particular significance is the fact that the augmentation system of the invention can be used in left and right side joint prostheses without modification.

The foregoing description of the illustrative embodiment of the invention is presented to indicate the range of constructions to which the invention applies. Variations in the physical architecture and dimensions of the augmentation system will be apparent to those having ordinary skill in the art based upon the disclosure herein, and such variations are considered to be within the scope of the invention in which patent rights are asserted, as set forth in the claims appended hereto.

What is claimed is:

1. An augmentation device for a joint prosthesis; comprising
   a main augmenting block adapted to mount on a surface of a joint prosthesis, the main augmenting block having a nominal distal surface and a proximal surface, first and second side surfaces that are either anterior or posterior surfaces, and third and fourth side surfaces that are either medial or lateral surfaces;
   a channel disposed in the main augmenting block and extending into an interior portion of the main augmenting block through one of the side surfaces of the main augmenting block;
   a secondary block means, adjustably positioned within the channel of the main augmenting block, for securing the augmentation device to a joint prosthesis, the secondary block means including a side surface that is either a lateral or medial surface and that corresponds in shape and orientation to the side surface of the main augmenting block through which the channel extends; and
   screw means associated with the secondary block means fog adjusting the position of the secondary block means relative to the main augmenting block between at least a first and a second position.

2. The device of claim 1 further including at least one surface feature selected from the group consisting of indentations and protrusions, said at least one surface feature being disposed on at least one of the side surfaces of the main block and being adapted to cooperate with a component of a joint prosthesis to secure the augmentation device to the joint prosthesis.

3. The device of claim 1 wherein the nominal distal surface of the main augmenting block has an area that is less than that of the proximal surface.

4. The device of claim 3 wherein the first and second side surfaces of the main augmenting block are canted.

5. The device of claim 2 wherein at least one surface feature is disposed on each of the third and fourth side surfaces of the main augmenting block.

6. The device of claim 2 wherein at least one surface feature is disposed on each of the first and second side surfaces of the main augmenting block.

7. The device of claim 2 wherein at least one surface feature is disposed on the side surface of the main augmenting block opposite the side surface of the main augmenting block through which the channel extends.

8. The device of claim 2 wherein at least one surface feature is disposed on the side surface of the main augmenting block opposite to the side surface of the main augmenting block through which the channel extends.

9. The device of claim 2 wherein at least one surface feature is disposed on the side surface of the secondary block means.

10. The device of claim 2 wherein the surface feature is a protrusion that extends outwardly and distally.

11. The device of claim 2 wherein the surface feature is an indentation that extends inwardly and proximally.

12. The device of claim 1 wherein the channel is open to the distal surface of the main augmenting block.

13. The device of claim 1 wherein the screw means extends into the interior of the secondary block means and is oriented substantially parallel to a medial-lateral plane of the main augmenting block.

14. The device of claim 1 wherein the device is able to be secured within a left or right side joint prosthesis.

15. The device of claim 14 wherein the joint prosthesis is a femoral component of an artificial knee joint.

16. The device of claim 1 further including a substantially centrally disposed aperture that extends from the nominal distal surface to the proximal surface.

17. The device of claim 16 further including a removable plug means for occluding the aperture, the plug means being disposed, in an interference fit, within the aperture of the main augmenting block.

18. The device of claim 1 wherein the first side surface is a posterior surface and the second side surface is an anterior surface having a length greater than the posterior surface.

19. The device of claim 18 wherein the proximal surface is of a convex, dome-like shape and is disposed opposite a distal surface that is angled from a distal end of the posterior surface to a distal end of the anterior surface.

20. A joint prosthesis, comprising
   a prosthesis component having a bone engaging surface and an opposed articulation surface;
   a main augmenting block adapted to mount upon the bone engaging surface of the prosthesis component, the main augmenting block having a nominal distal surface which contacts the bone engaging surface and a proximal surface, first and second side surfaces that are either anterior or posterior surfaces, and third and fourth surfaces that are either medial or lateral surfaces;
   a channel disposed in the main augmenting block and extending into an interior portion of the main augmenting block through one of the side surfaces of the main augmenting block;
   a secondary block means, adjustably positioned within the channel of the main augmenting block, for securing the augmentation device to a joint prosthesis, the secondary block means including a side surface that is either a lateral or medial surface and that corresponds in shape and orientation to the side surface of the main augmenting block through which the channel extends; and
   screw means associated with the secondary block means for adjusting the position of the secondary block means relative to the main augmenting block.

21. The joint prosthesis of claim 20 wherein the prosthesis component is a femoral component of a knee joint prosthesis.

* * * * *